(12) United States Patent
Muller et al.

(10) Patent No.: US 10,207,016 B2
(45) Date of Patent: Feb. 19, 2019

(54) SAMPLE PREPARATION CONTAINER

(71) Applicant: Merck Patent GmbH, Darmstadt (DE)

(72) Inventors: Gerard Muller, Urmatt (FR); Mathieu Arrault, Dabo (FR)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/519,201

(22) PCT Filed: Sep. 16, 2015

(86) PCT No.: PCT/EP2015/001853
§ 371 (c)(1),
(2) Date: Apr. 14, 2017

(87) PCT Pub. No.: WO2016/058662
PCT Pub. Date: Apr. 21, 2016

(65) Prior Publication Data
US 2017/0224860 A1 Aug. 10, 2017

(30) Foreign Application Priority Data
Oct. 15, 2014 (EP) ..................... 14290310

(51) Int. Cl.
*A61L 2/28* (2006.01)
*B01D 65/02* (2006.01)
(Continued)

(52) U.S. Cl.
CPC ............... *A61L 2/28* (2013.01); *B01D 65/02* (2013.01); *C12Q 1/22* (2013.01); *B01L 3/5082* (2013.01);
(Continued)

(58) Field of Classification Search
CPC ..... A61L 2/28; B01D 65/02; B01L 2200/026; B01L 2300/0832; B01L 3/5082; C12Q 1/22
See application file for complete search history.

(56) References Cited

U.S. PATENT DOCUMENTS 4,036,698 A * 7/1977 Bush .................. C12Q 1/22
435/287.4
4,215,198 A 7/1980 Gordon
(Continued)

FOREIGN PATENT DOCUMENTS

DE 10015788 A1 10/2001
EP 2089161 B1 11/2011
(Continued)

OTHER PUBLICATIONS

International Search Report dated Dec. 8, 2015 issued in corresponding PCT/EP2015/001853 application (4 pages).
(Continued)

*Primary Examiner* — Gautam Prakash
*Assistant Examiner* — Lydia Edwards
(74) *Attorney, Agent, or Firm* — Millen White Zelano and Branigan, PC; Csaba Henter

(57) ABSTRACT

A sample preparation container, preferably for use in sterility testing, comprising a housing (1) having a housing wall (2) defining an inside space (3), a support on which a membrane filter is placed or is to be placed so as to get in contact with a sampling fluid to be introduced into the inside space (3), and at least one inlet opening (4) to the inside space (3) and at least one outlet opening from the inside space (3). A sampling port (5) is provided for allowing access from the outside to the inside space (3), wherein said sampling port (5) is closed by a septum (6) and the septum (6) is separated from the inside space (3) by a barrier wall (7) which is preferably piercable or breakable on application
(Continued)

of an external force, preferably applied through a sampling instrument like a needle (8).

13 Claims, 3 Drawing Sheets

(51) Int. Cl.
 *C12Q 1/22* (2006.01)
 *B01L 3/00* (2006.01)
(52) U.S. Cl.
 CPC . *B01L 2200/026* (2013.01); *B01L 2300/0832* (2013.01)

(56) References Cited

U.S. PATENT DOCUMENTS

| | | | |
|---|---|---|---|
| 5,516,648 | A | 5/1996 | Malchesky et al. |
| 6,410,308 | B2 | 6/2002 | Hendel |
| 7,674,434 | B2 | 3/2010 | Sakal et al. |
| 2001/0031494 | A1 | 10/2001 | Hendel |
| 2008/0121050 | A1 | 5/2008 | Sakal et al. |
| 2009/0117646 | A1 | 5/2009 | Stordeur et al. |
| 2017/0002395 | A1 | 1/2017 | Baumstummler et al. |

FOREIGN PATENT DOCUMENTS

| | | |
|---|---|---|
| WO | 96/06184 A1 | 2/1996 |
| WO | 2010/043271 A1 | 4/2010 |
| WO | 2015/096885 A1 | 7/2015 |

OTHER PUBLICATIONS

Written Opinion of the International Searching Authority dated Dec. 8, 2015 issued in corresponding PCT/EP2015/001853 application (6 pages).

\* cited by examiner

Prior Art

SAMPLE PREPARATION CONTAINER

The invention relates to a sample preparation container, preferably for use in the field of sample preparation and detection for sterility testing. It is also applicable for process testing and final product testing in the pharmaceutical and biotech industries.

TECHNICAL BACKGROUND

A sample preparation container of the type and for the field of use to which the present invention generally pertains is disclosed in the document U.S. Pat. No. 4,036,698 B. The sample preparation container disclosed in this document is shown in FIG. 4. The sample preparation container is intended for testing solutions such as antibiotic solutions to determine the presence of microorganisms, in which the solution is flowed through a container having a microporous membrane filter which strains microorganisms from the solution and concentrates them on the membrane filter. Thereafter, the container is flushed with a sterile solution, followed by filling the container with an appropriate growth culture medium with the filter being vented, during this step, through a vent having a hydrophobic filter to prevent intake of bacteria. The presence of microorganisms in the original solution to be tested is normally determined by visual observation of the turbidity of the growth solution after an appropriate incubation period at suitable temperature. For certain testing steps access to the inside space of the container is required, for example by a sampling instrument including a syringe or the like. For this purpose an additional suitable sampling port is provided on the container.

The sample preparation container disclosed in the document U.S. Pat. No. 4,036,698 B shown in FIG. 4 is in the form of a canister 11 formed as a right cylinder, preferably of a transparent material such as plastics like a clear plexiglas. At one end of the canister 11 there are two ports 13 and 15, wherein the port 15 is provided with a removable sealing cap 17 and the port 13 is or is to be connected with a tube for samples and media transfer. Port 15 includes a hydrophobic microporous filter which is typically formed of cellulose esters coated with a hydrophobic material and performs the function of filtering of all microorganisms above a specific size from the air flow through the filter. The opposite end of the canister 11 is closed with a base member 32, in which a third port 21 is located and this port is also provided with a removable sealing cap 22. A membrane filter 26 which extends substantially the full diameter of the canister 11 is located at the junction between the cylinder wall 30 of the canister 11 and the base member 32. This filter 26 is positioned generally parallel to the ends of the canister 11 and is sealed at its periphery to the wall 30 of the canister. The material and porosity of filter is determined according to the size of the microorganisms to be detected.

Although this sample preparation container is described here as an example of a typical sample container for use in sterility testing and thus of a type to which the invention pertains, modifications of the container in details are possible within the concept of the invention to the extent that they are not related to the function of the sampling port. The method of using the sample preparation container for sterility testing as described in the document U.S. Pat. No. 4,036,698 B is introduced herein by reference.

Although the sampling port in this prior art is sealed with a removable ceiling cap, the existence of even minimal death cavities between the inside space of the container and the sampling port can lead to a retention of antibiotics even after the rinsing step and can cause false negative testing results. Further, the access to the inside space though the sampling port can lead to contamination of the sample even if it is performed under sterile conditions. Further, repeated access through the sampling port increases the risk of contamination of the sample.

It is the object of the invention to provide a further improved sample preparation container, preferably for sterility testing.

To solve the problem the invention provides, preferably for sterility testing, a sample preparation container as defined by claim 1. Preferred embodiments of the sample preparation container are defined in the dependent claims and will become apparent from the following description. According to an aspect of the present invention a sample preparation container specifically comprises a housing having a housing wall defining an inside space, a support on which a membrane filter is placed or is to be placed so as to get in contact with a sampling fluid to be introduced into the inside space, at least one inlet opening to the inside space and at least one outlet opening from the inside space, and a sampling port for allowing access from the outside to the inside space, wherein said sampling port is closed by a septum and the septum is separated from the inside space by a barrier wall.

In that the sampling port of the container is closed by the septum a contamination of the sample inside the container can be avoided when a sampling device like a needle or the like is inserted from the outside to get access to the inside space, i.e. to extract fluid from the inside space or to add any fluid to the inside space. The septum also allows repeated access in a sterile manner, especially if the septum has self-sealing properties in general, preferably if the septum is in the form of a block of piercable material that has such a self-sealing property. Since the septum is further separated from the inside space by a barrier wall the contact between the septum and the sample inside the container can be excluded at least as long as the barrier wall remains intact. This avoids death cavities where substances like antibiotics could be retained following rinsing with fluid or other steps of the process where the container is used (i.e. concentration steps and media insertion). This considerably reduces the risk of false negative test results. Further, the barrier wall also eliminates the risk of material migration from the septum to the sample which could be another source of false testing.

Preferably the barrier wall is continuous/seamless with a part of the housing wall and the barrier wall is preferably integrally formed with a part of the housing wall. This design further reduces the problem of material retention in crevasses of the container wall and provides a very cost effective way of producing the container.

Preferably the integrally formed barrier wall is formed as a thinned part of the housing wall preferably such that the barrier wall is prepiercable or breakable on application of an external force, preferably applied through a sampling instrument like a needle. With this design the barrier wall can be easily pierced or broken at a defined location to allow access to the inside space by means of a suitable instrument like the syringe or a sharp tip.

Preferably the barrier wall has a preformed piercing location and/or tear line, preferably formed on the side facing the septum. With this design the process of rupture of the wall can be controlled so that not only the force required to open the barrier wall can be predefined but also that the forming of fragments can be controlled, for example such that the fragments remain attached to the periphery of the opening and are not separated from the container wall.

Preferably at least the part of the container wall in the vicinity of and, optionally, including the barrier wall is rigid or flexible. This design provides a possibility of using a generally flexible container but to make a portion including the barrier wall relatively more rigid to allow the introduction of the force required to break and open the sampling port, or, to have a generally rigid container and to render the portion including the barrier wall relatively more flexible to facilitate the opening.

Preferably the septum is located in a holding space adjacent to the barrier wall. With this design the septum is safely held in a defined location during transport and handling and especially during the sampling operation. It also facilitates the manufacturing of the container since the septum that is typically made from a different material than the container wall can be subsequently inserted into the holding defined space. The holding space can be integrally formed with the housing wall which is particularly cost effective or it can be formed in an insert that includes the barrier wall. In the latter case the holding space can be more easily added to existing container designs where the mold for forming the container does not allow the integral forming. The insert can be bonded or otherwise sealed to an opening in the container wall. This design is particularly useful where the insert and container are of different materials (i.e. flexible vers. rigid or different material compositions). It also facilitates processing like recycling of spent containers.

Preferably the septum is in the form of a block of piercable material and is held in the space by a form-locking protrusion. This design facilitates the subsequent insertion of the septum after manufacturing of the container and reliably secures the septum in place even against forces trying to withdraw the septum from the space when a sampling instrument (i.e. a syringe) is withdrawn.

Preferably the septum is arranged adjacent to the barrier wall substantially without any void volume located therebetween. This feature considerably contributes to the avoiding of material retention especially after the barrier wall has been broken once during a sampling operation.

In an alternative design the septum is arranged on the sampling port, preferably in the form of a cap that surrounds at least part of the periphery of the sampling port. This design provides the advantage that the canister sterility is even more safely maintained because it is less likely and more difficult for contaminants to migrate through the interface between the septum and the housing material since the septum surrounds the port is located on the outside of the port.

In this alternative design the septum can be arranged on the sampling port such that a cavity is formed between the septum and the barrier wall. The needle or any other instrument used to pierce the septum and the barrier wall can be guided through this cavity and there is thus no risk that the force imparted on the septum though the needle, i.e. by friction or lateral movements causes the septum to dislocate from contact with the lateral side wall of its receptacle that could open an undesired path for ingress of contamination.

In order to avoid contamination and/or damaging of the septum during transport, storage and handling the septum can be protected from contact with the outside environment by means of a removable cap or seal.

BRIEF DESCRIPTION OF THE DRAWINGS

These and other aspects will become apparent from the description of preferred embodiments described below in connection with the attached drawing. In this drawing.

Figure 1:
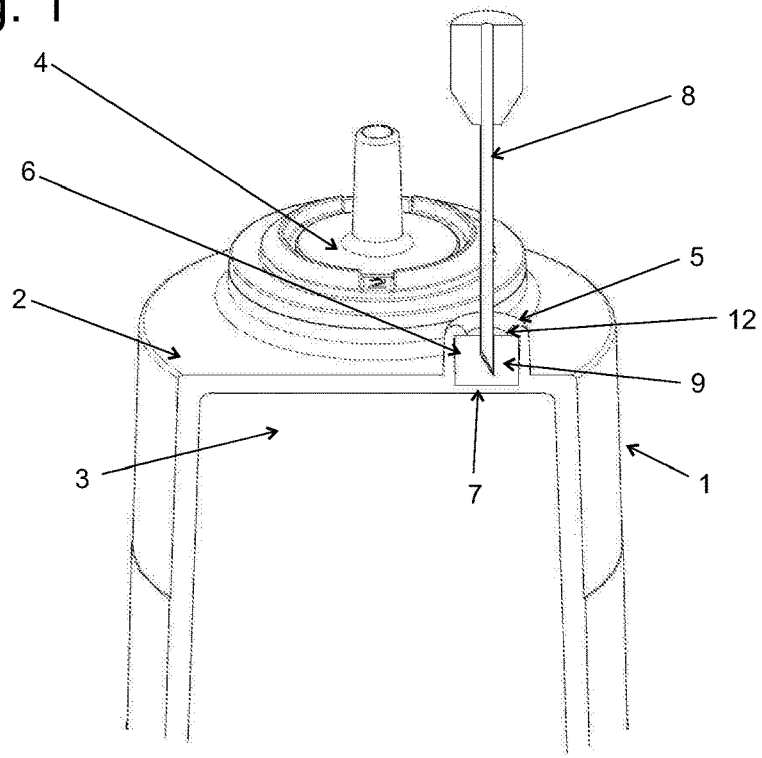
FIG. 1 is a perspective partial cross-sectional view of a sample preparation container according to an embodiment of the invention where a needle is partly inserted into a septum.
Figure 2:
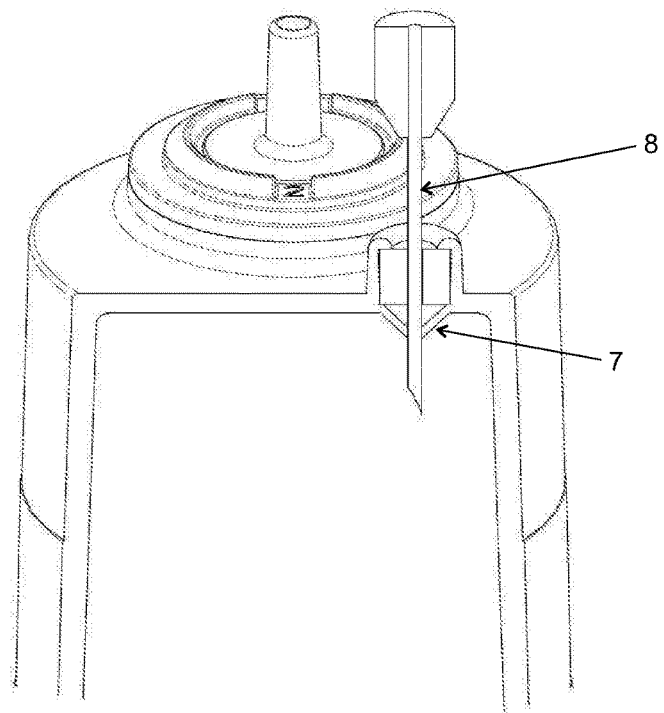
FIG. 2 is a perspective partial cross-sectional view of the sample preparation container of FIG. 1 where the needle is fully inserted into an inside space.
Figure 4:
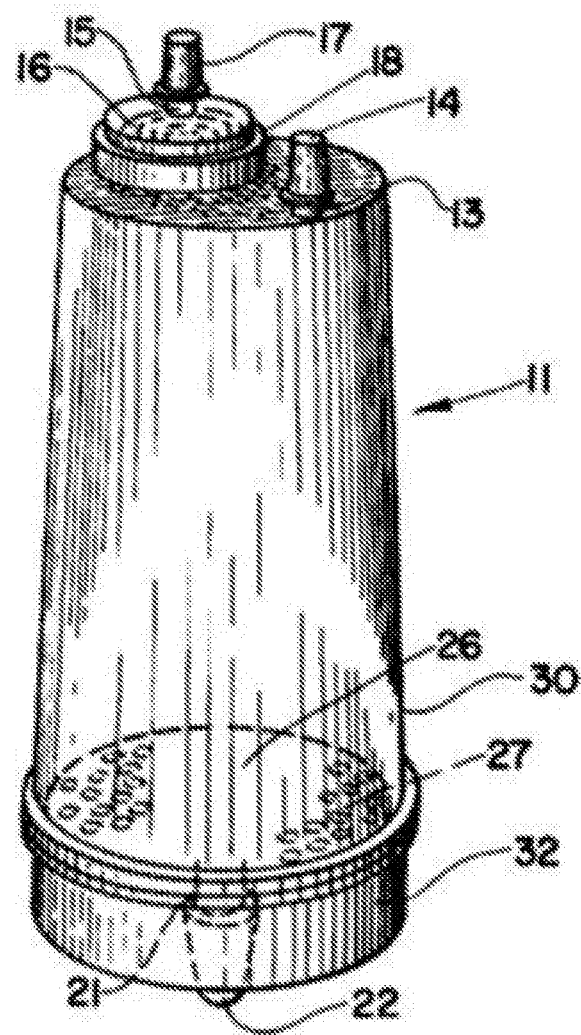
FIG. 4 is a perspective view of a known sample preparation container.

An example of a preferred embodiment of a sample preparation container of the invention is shown in FIGS. 1 and 2 at two stages of use in a sampling operation. The Figs. only show a part of the upper section of the container with details other than those related to the sampling port being omitted. The further features of the sampling container can be the same as or similar to those in the prior art of such containers, for example those described in connection with FIG. 4.

The housing 1 of the sample preparation container has a housing wall 2 defining an inside space 3. A support (not shown) on which a membrane filter is placed or is to be placed so as to get in contact with the sampling fluid to be introduced to the inside space 3 is formed inside the container (for example as shown and described in connection with the prior art of FIG. 4). The sample preparation container of the invention like the one shown in FIG. 4 has at least one inlet opening 4 to the inside space 3 and at least one outlet opening (not shown) from the inside space 3.

A sampling port 5 is provided for allowing access from the outside to the inside space 3. The sampling port 5 includes a septum 6, preferably in the form of a block of piercable material which has self-sealing properties and which is held in a space 9 defined by a cylindrical wall protruding from the housing wall, for example at an upper end of the housing 1. The cylindrical wall surrounds a barrier wall 7 which separates the septum 6 from the inside space 3 of the container. The barrier wall 7 is integrally formed with the housing wall 2 and, in this case, is formed as a thinned part of the housing wall 2. There are preferably no crevasses or cracks or other protrusions or recesses on the inside wall as the barrier wall 7 is continuous/seamless with the part of the housing wall were it is formed.

Due to the thin wall thickness the barrier wall is more easily piercable or breakable on application of an external force, preferably applied through a sampling instrument like a needle or syringe 8. In FIG. 1 the needle is shown partially inserted through the septum 6 but not yet through the barrier wall 7. In order to facilitate breaking/opening of the barrier wall with a defined force and with a defined retaining of fragments to the peripheral wall the barrier wall 7 is preferably formed with a preformed piercing location and/or tear line or lines, which are preferably formed on the side facing the septum in order to avoid crevasses or protrusions on the side facing the inside space.

The holding space 9 for the septum defined by the cylindrical protruding wall is located adjacent the barrier wall 7. The FIG. 2 shows a situation where the needle is fully inserted through the septum and through the barrier wall. As shown, the fragments of the barrier wall still adhere to the container at the periphery and preferably are in close contact to the outside of the needle due to their resiliency to maintain tight contact to reduce the risk of ingress of contaminants. Pulling out of the needle from the sampling port will at least partly restore the fragments of the barrier wall into their initial orientation but will of course not fully close the sampling port. The material properties and structure of the septum provide for the re-sealing of the sampling port.

The septum 6 is arranged adjacent and close to the barrier wall 7 substantially without any void volume located there between in order to reduce the potential retaining spaces or crevasses for a situation after the sampling port has once been opened.

The outside periphery of the cylindrical wall defining the holding space 9 is formed with a form-locking protrusion 12 protruding radially inside from the wall. This protrusion allows subsequent insertion of the septum after forming of the container and avoids that the septum is inadvertently withdrawn from the holding space 9 together with the sampling instrument. The dimensions of the block of the septum and the size of the space 9 can be adapted such that the septum, once inserted is maintained in an elastically deformed state such that it is constantly tightly pressed against the barrier wall in order to reduce any void volume. Other forms of protrusions are possible like plural inward-protruding teeth spaced about the periphery. A separate element, i.e. a flange, mechanically fixing the septum in the holding space can be provided instead of an integrated holding feature. The rounded or chamfered rim bordering the radial inner end of the protrusion 12 facilitates insertion of the septum.

Figure 3:
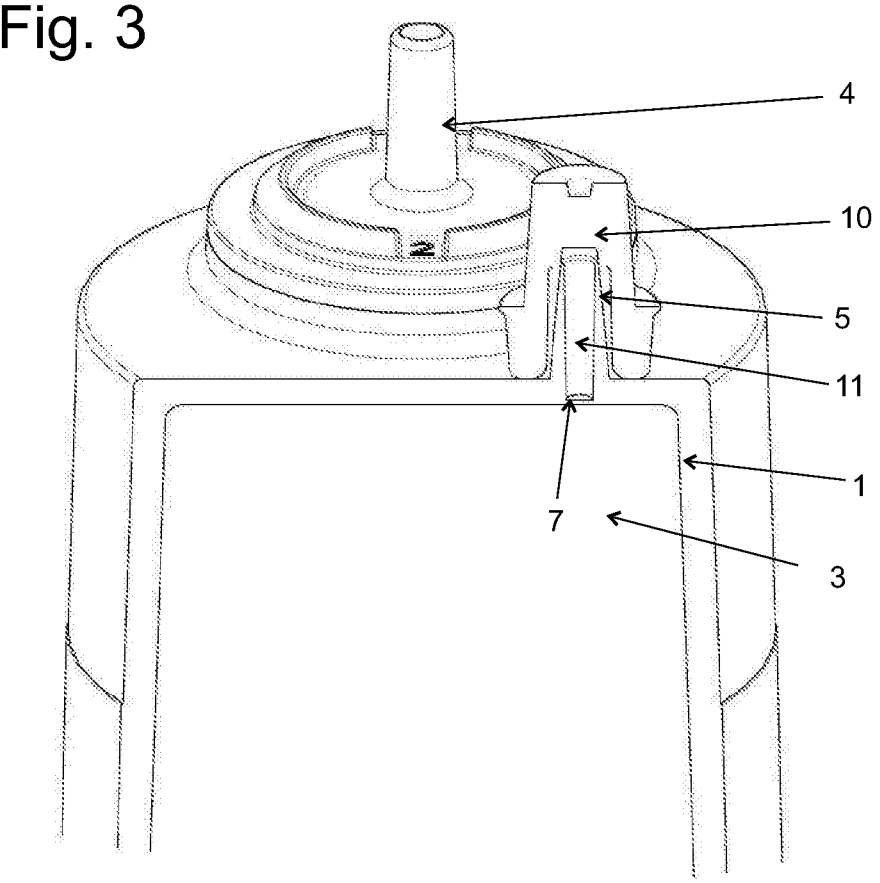
FIG. 3 is a perspective partial cross-sectional view of the sample preparation container according to an alternative design where the needle is inserted through the septum but not yet through the barrier wall.

FIG. 3 is a perspective partial cross-sectional view of a sample preparation container according to an alternative design where the septum 10 is arranged on the sampling port 5, preferably in the form of a cylindrical cap that surrounds at least part of the periphery of the sampling port 5. The port 5 in this case is a cylindrical wall or other form of protrusion formed on the upper wall of the container 1. Preferably the septum in this design surrounds and covers the entire outer periphery of the protrusion to maximize the sealing effect. The inner volume of the protrusion in the alternative design as shown is not filled with the septum 10 but is in the form of a cavity 11 that is formed between the septum 10 and the barrier wall 7. However, the septum in the form of a cylindrical cap can be provided with an inner stem or plug (not shown) that is at least partly inserted into the cavity.

The alternative design having the septum arranged on the sampling port, i.e. on the outside thereof, provides an advantage that a needle 8 or any other instrument used to pierce the septum and the barrier wall can be guided through the cavity 11, even if it is partly filled with septum material, and there is thus no risk that a force imparted on the septum though the needle, i.e. by friction or lateral movements causes the septum to dislocate from contact with the lateral side wall of its receptacle that could open an undesired path for ingress of contaminants from the outside. Thereby, the septum will even further contribute to maintaining the sterility of the container even after it has been pierced once. The other properties of the septum are the same as those described in connection with FIGS. 1, 2 and 4.

Although not shown the sampling port including the septum can be protected from contact with the outside environment of the container by means of a removable cap or seal that can be connected to the outer periphery of the wall defining the holding space 9 and/or to the top axial end surface of this wall and/or on the outer periphery of the septum in the case where this is already placed on the port as described above, i.e. by a threaded engagement, a frictional fit or a bonding connection.

Although the barrier wall 7 as well as the wall defining the holding space 9 for the septum 6 are shown to be integrally formed with the material of the container, these elements could be formed in the form of a separate insert that is either insert-molded with the material of the container at an appropriate location or is attached to an opening of the housing wall after the same has been formed. In this case the transition between the insert and the inner wall of the container should of course be sealed to avoid the crevasses or gaps that could retain antibiotics leading to potentially false testing results.

For the material of the container and for the septum any known materials used in the field can be used. The container can be made from a flexible material or from a rigid or semi-rigid material. The material and properties of the barrier wall and, if desired, of a certain periphery thereof can be different from those of the rest of the container. For example, while the container can be flexible in the form of a bag, the barrier wall and a part of its periphery can be relatively more rigid to withstand the forces when the sampling instrument is inserted to pierce the septum and rupture the barrier wall. The holding space for the septum can be formed with the more rigid barrier wall as well. Vice versa the barrier wall can be relatively more flexible as compared to a rigid container wherein this property could be achieved by sufficiently thinning out the barrier wall as compared to the thickness of the wall of the container.

The invention claimed is:

1. A sample preparation container, comprising
   a housing (1) having a housing wall (2) defining an inside space (3),
   a support on which a membrane filter is placed so as to get in contact with a sampling fluid to be introduced into the inside space (3),
   at least one inlet opening (4) to the inside space (3) and at least one outlet opening from the inside space (3), and
   a sampling port (5) for allowing access from the outside to the inside space (3),
   wherein said sampling port (5) is closed by a septum (6;10) and the septum (6;10) is separated from the inside space (3) by a barrier wall (7),
   wherein the barrier wall (7) is pierceable or breakable on application of an external force,
   wherein the barrier wall (7) is continuous/seamless with a part of the housing wall (2), and
   wherein the septum (6) is arranged adjacent to the barrier wall (7) substantially without any void volume located therebetween.

2. The sample preparation container according to claim 1, wherein the barrier wall (7) is integrally formed with a part of the housing wall (2).

3. The sample preparation container according to claim 2, wherein the barrier wall (7) is formed as a thinned part of the housing wall (2).

4. The sample preparation container according to claim 1, wherein at least the part of the container wall (2) in the vicinity of and, optionally, including the barrier wall (7) is rigid or flexible.

5. The sample preparation container according to claim 1, wherein the septum (6) is located in a holding space (9) adjacent to the barrier wall (7).

6. The sample preparation container according to claim 5, wherein the holding space (9) is integrally formed with the housing wall (2) or is formed in an insert that also includes the barrier wall (7).

7. The sample preparation container according to claim 5, wherein the septum (6) is in the form of a block of pierceable material and is held in the space (9) by a form-locking protrusion (12).

8. The sample preparation container according to claim 1, wherein the septum (6) is protected from contact with the outside environment by a removable cap or seal.

9. The sample preparation container according to claim 1, wherein the barrier wall (7) is pierceable or breakable on application of an external force applied through a sampling instrument.

10. The sample preparation container according to claim 1, wherein the barrier wall (7) is pierceable or breakable on application of an external force applied through a sampling instrument that is a needle (8).

11. The sample preparation container according to claim 1, wherein the barrier wall (7) has a preformed piercing location and/or tear line formed on the side facing the septum (6;10).

12. A sample preparation container, comprising a housing (1) having a housing wall (2) defining an inside space (3), a support on which a membrane filter is placed so as to get in contact with a sampling fluid to be introduced into the inside space (3), at least one inlet opening (4) to the inside space (3) and at least one outlet opening from the inside space (3), and a sampling port (5) for allowing access from the outside to the inside space (3), wherein said sampling port (5) is closed by a septum (6;10) and the septum (6;10) is separated from the inside space (3) by a barrier wall (7), wherein the barrier wall (7) is pierceable or breakable on application of an external force, wherein the barrier wall (7) is continuous/seamless with a part of the housing wall (2), and wherein the septum (6) is arranged adjacent to the barrier wall (7) substantially without any void volume located therebetween, wherein the barrier wall (7) is pierceable or breakable on application of an external force, and the barrier wall (7) has a preformed piercing location and/or tear line.

13. A sample preparation container, comprising a housing (1) having a housing wall (2) defining an inside space (3), a support on which a membrane filter is placed so as to get in contact with a sampling fluid to be introduced into the inside space (3), at least one inlet opening (4) to the inside space (3) and at least one outlet opening from the inside space (3), and a sampling port (5) for allowing access from the outside to the inside space (3), wherein said sampling port (5) is closed by a septum (6;10) and the septum (6;10) is separated from the inside space (3) by a barrier wall (7), wherein the barrier wall (7) is pierceable or breakable on application of an external force, wherein the barrier wall (7) is continuous/seamless with a part of the housing wall (2), and wherein the septum (6) is arranged adjacent to the barrier wall (7) substantially without any void volume located therebetween, wherein the septum (6) is in the form of a block of pierceable material that has a self-sealing property.

* * * * *